(12) United States Patent
Oleson et al.

(10) Patent No.: US 9,808,701 B2
(45) Date of Patent: Nov. 7, 2017

(54) WEARABLE DATA HUB

(71) Applicant: Under Armour, Inc., Baltimore, MD (US)

(72) Inventors: Mark A. Oleson, Baltimore, MD (US); F. Grant Kovach, Baltimore, MD (US); Nathan Dau, Baltimore, MD (US); Angela Nelligan, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 19 days.

(21) Appl. No.: 14/947,412

(22) Filed: Nov. 20, 2015

(65) Prior Publication Data

US 2017/0144051 A1    May 25, 2017

(51) Int. Cl.
| | |
|---|---|
| G08B 21/22 | (2006.01) |
| A63B 71/06 | (2006.01) |
| A63B 24/00 | (2006.01) |
| A43B 5/00 | (2006.01) |
| A43B 3/00 | (2006.01) |
| A63B 22/02 | (2006.01) |
| A63B 22/06 | (2006.01) |
| A63B 21/06 | (2006.01) |

(52) U.S. Cl.
CPC ........ A63B 71/0619 (2013.01); A43B 3/0005 (2013.01); A43B 5/00 (2013.01); A63B 21/06 (2013.01); A63B 22/02 (2013.01); A63B 22/0605 (2013.01); A63B 24/0062 (2013.01); A63B 2220/12 (2013.01); A63B 2225/50 (2013.01)

(58) Field of Classification Search
CPC ............ A63B 2225/50; A63B 2225/15; A63B 24/0062
USPC ................... 340/539.23, 539.13, 686.6, 86.1
See application file for complete search history.

(56) References Cited

U.S. PATENT DOCUMENTS

| | | | |
|---|---|---|---|
| 2013/0178334 A1* | 7/2013 | Brammer ........... | A63B 71/0622 482/4 |
| 2013/0297669 A1* | 11/2013 | Wang .................... | G06F 19/345 709/201 |
| 2016/0082317 A1* | 3/2016 | Doherty ............. | A63B 24/0062 340/870.07 |

* cited by examiner

Primary Examiner — Kevin Kim

(57) ABSTRACT

A wearable device includes: a wake up component that generates a first wake-up signal based on a first detected exercise activity location and generates a second wake-up signal based on a second detected exercise activity location; a receiver that receives a first exercise signal from a first transmitter based on receipt of the first wake-up signal and receives a second exercise signal from a second transmitter based on receipt of the second wake-up signal, the first exercise signal being associated with a first exercise session of the user, the second exercise signal being associated with a second exercise session of the user; a memory that stores first exercise data based on first exercise signal and stores second exercise data based on the second exercise signal; and a transmitter that transmits an exercise download signal based on the first exercise data and the second exercise data.

20 Claims, 4 Drawing Sheets

US 9,808,701 B2

WEARABLE DATA HUB

BACKGROUND

The present invention generally relates to devices and methods for downloading and displaying information.

There exists a need for a device and method to download and display information related to a user's activities.

BRIEF SUMMARY OF THE DRAWINGS

The accompanying drawings, which are incorporated in and form a part of the specification, illustrate example embodiments and, together with the description, serve to explain the principles of the invention. In the drawings.

DETAILED DESCRIPTION

Overview

A wearable device is provided for use by a user. The wearable device, includes a wake up component, a receiver, a memory and a transmitter. The wake up component generates a first wake-up signal based on a first detected exercise activity location and generates a second wake-up signal based on a second detected exercise activity location. The receiver receives a first exercise signal from a first transmitter based on receipt of the first wake-up signal and receives a second exercise signal from a second transmitter based on receipt of the second wake-up signal. The first exercise signal is associated with a first exercise session of the user, and the second exercise signal is associated with a second exercise session of the user. The memory stores first exercise data based on first exercise signal and stores second exercise data based on the second exercise signal. The transmitter transmits an exercise download signal based on the first exercise data and the second exercise data.

Example Embodiments

One of the recent trends in fitness is using a wearable device to record data related to the activity a user is performing. The data can be downloaded directly to a computer, smartphone, or other smart device, and the user can refer to the downloaded data to track his progress. A conventional wearable device may incorporate various sensors to determine activity levels. Non-limiting examples of such sensors include temperature sensors, pressure sensors, water sensors, moisture sensors, saline sensors, electric field sensors, current sensors, voltage sensors, impedance sensors, magnetic field sensors, accelerometers, altimeters, GPS sensors, magnetometers, optical sensors, and chemical sensors.

Traditionally, a user may wear one or more wearable devices to record data from the activities in which the user is participating. However, issues may arise when one or more of the sensors incorporated into the wearable device break or become corrupted. The data the wearable device records, if it records any at all, will be unreliable and may cause considerable user displeasure. There exists a need for a more streamlined wearable device that receives, rather than generates, information related to a user's activity levels.

Figure 1:
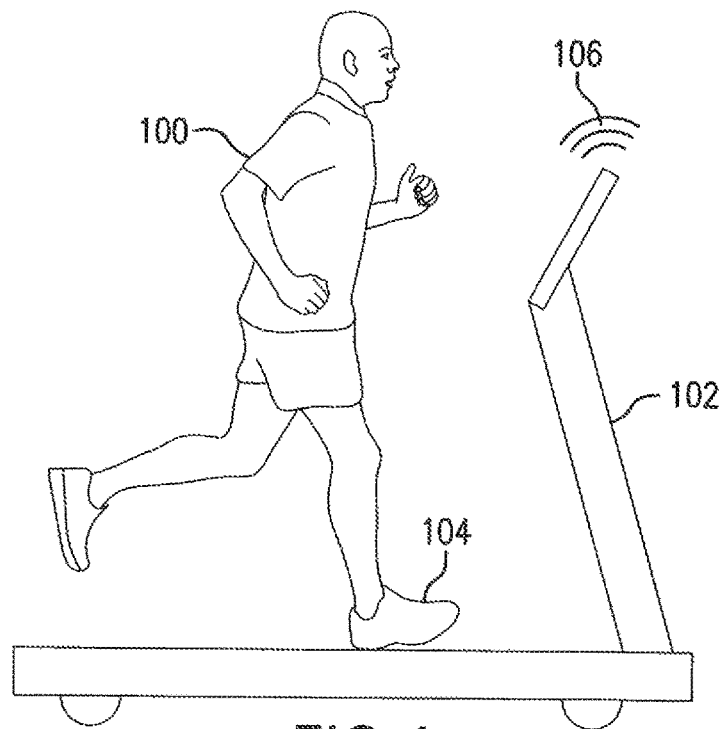
FIG. 1 illustrates an exercise machine transmitting information to a wearable device while a user is running.

FIG. 1 illustrates an exercise machine transmitting information to a wearable device while a user is running.

As shown in the figure, user 100 is running on treadmill 102. User 100 is wearing shoes 104 while running.

Similar to a conventional treadmill, treadmill 102 is operable to provide user 100 with the desired workout parameters based on the input of user 100. The parameters may include speed, incline, intervals, and any other parameters that are typically available on a conventional treadmill. Treadmill 102 is also operable to transmit a data signal related to the workout of user 100 to a wearable device via wireless connection 106, such that the wearable device can receive and store the data signal. The data signal may include the raw data generated by treadmill 102, but it also may include a function of the raw data generated by treadmill 102.

Shoes 104 are similar to conventional workout shoes; however, shoes 104 are also operable to receive data signals from exercise equipment like treadmill 102, where the data signals are related to the workout activity the user is performing. Shoes 104 are an example of a smart wearable device, which is a device that incorporates a computer chip into its design. The computer chip typically includes sensors, a memory that can store the data the sensors record, and a transmitter/receiver so that data, or functions thereof, can be uploaded/downloaded. The computer chip in shoes 104, however, may not include sensors as the chip is designed to receive, store, and transmit data. The receiver can receive data from exercise equipment, like treadmill 102, and store it in the memory. The computer chip may also manipulate the data signals to generate a signature that is a function of the data. Signatures may include, but are not limited to: amount of work done, change in calories burned over time, and change in gait length over time.

In order to view the recorded data signals and signatures, shoes 104 must be tethered or otherwise connected to another device, as shoes 104 do not provide user 100 with a way to view the data signals or signatures. In many instances, shoes 104 are tethered (via a wireless or wired connection) to a smartphone so a user can upload the data to the phone follow the progress of his exercise regimen. In other embodiments, shoes 104 may be tethered to a computer (via a wireless or wired connection). In yet other embodiments, shoes 102 may be tethered (via a wireless or wired connection) to another smart device, like a smart television.

Figure 2:
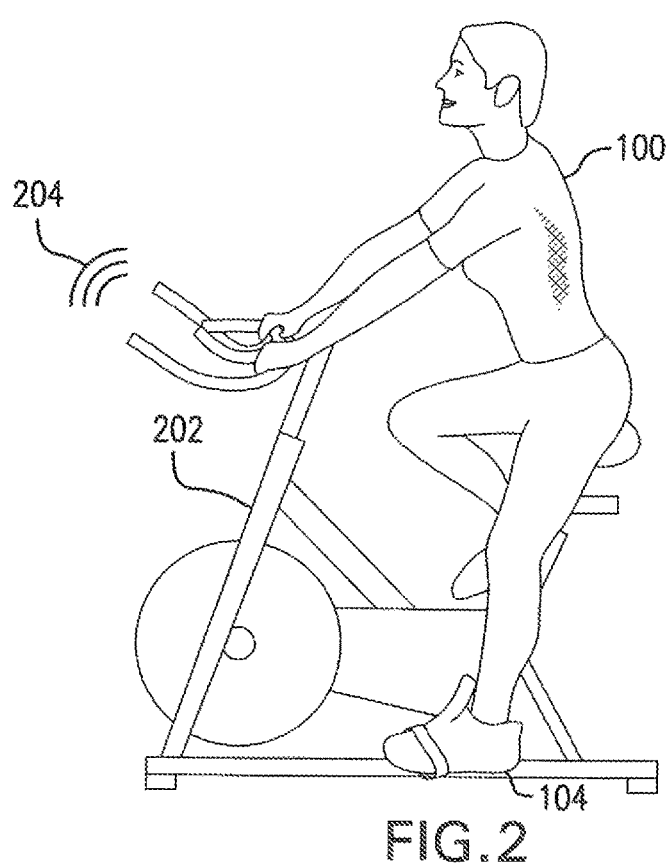
FIG. 2 illustrates another exercise machine transmitting information to a wearable device while a user is biking.

FIG. 2 illustrates another exercise machine transmitting information to a wearable device while a user is biking;

As shown in the figure, user 100 is using stationary bike 202. User 100 is wearing shoes 104 while biking.

Similar to a conventional stationary bike, stationary bike 202 is operable to provide user 100 with the desired workout parameters based on the input of user 100. The parameters may include speed, incline, intervals, and any other parameters that are typically available on a conventional stationary bike. Stationary bike 202 is also operable to transmit a data signal related to user 100's workout to shoes 104 via wireless connection 204, in a manner similar to how treadmill 102 transmits data to shoes 104, as discussed above. The data signal may include the data generated by stationary bike 202, but it also may include signatures based on the data generated by stationary bike 202.

Figure 3:
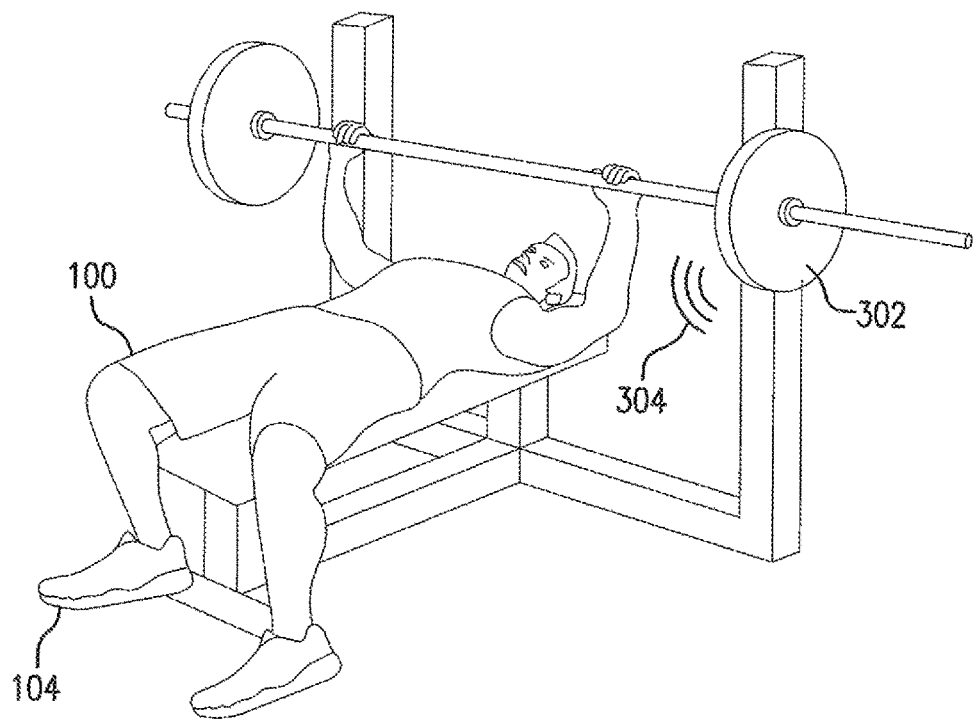
FIG. 3 illustrates another exercise machine transmitting information to a wearable device while a user is lifting weights.

FIG. 3 illustrates another exercise machine transmitting information to a wearable device while a user is lifting weights.

Similar to a conventional weightlifting apparatus, weightlifting apparatus 302 is operable to provide user 100 with the desired workout parameters based on the input of user 100. The parameters may include weight, number of repetitions, number of sets, and any other parameters that may be recorded by a weightlifting apparatus. Weightlifting apparatus 302 is also operable to transmit a data signal related to user 100's workout shoes 104 via wireless connection 304, as discussed above. The data signal may include the data generated by weightlifting apparatus 302, but it also may include signatures based on the data generated by weightlifting apparatus 302.

Figure 4:
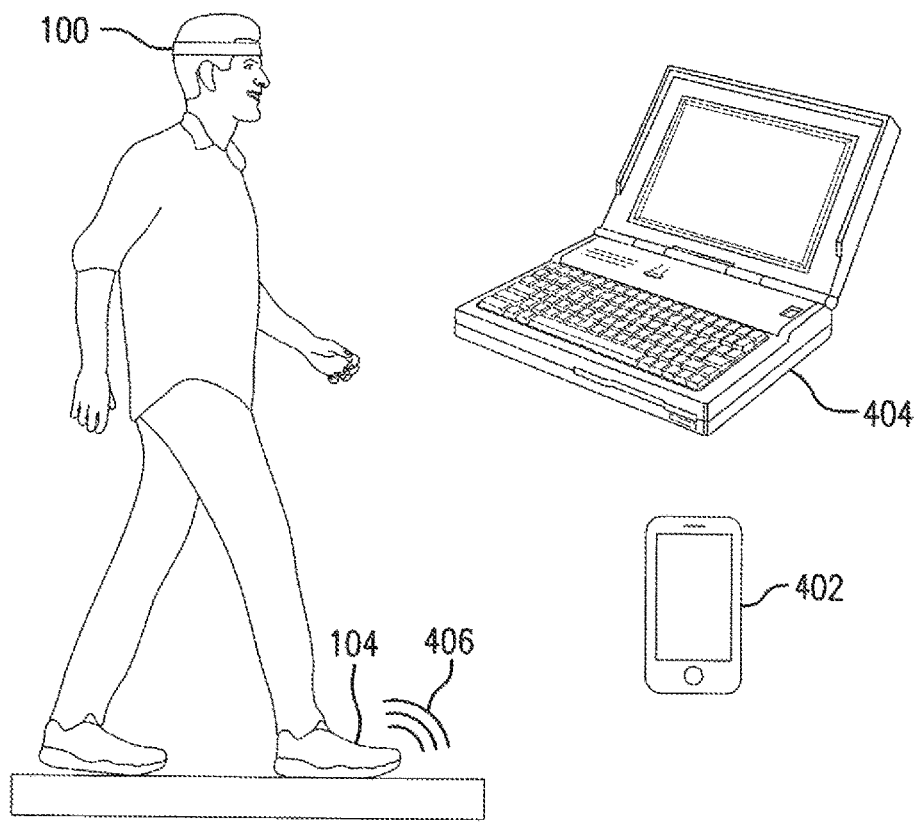
FIG. 4 illustrates downloading the information from the wearable device to another device in accordance with aspects of the present invention.

FIG. 4 illustrates downloading the information from the wearable device to another device in accordance with aspects of the present invention;

As shown in the figure, user 100 is wearing shoes 104 and is in the vicinity of mobile phone 402 and computer 404.

The operation of shoes 104 will be further described with reference to FIGS. 5-6.

Figure 5:
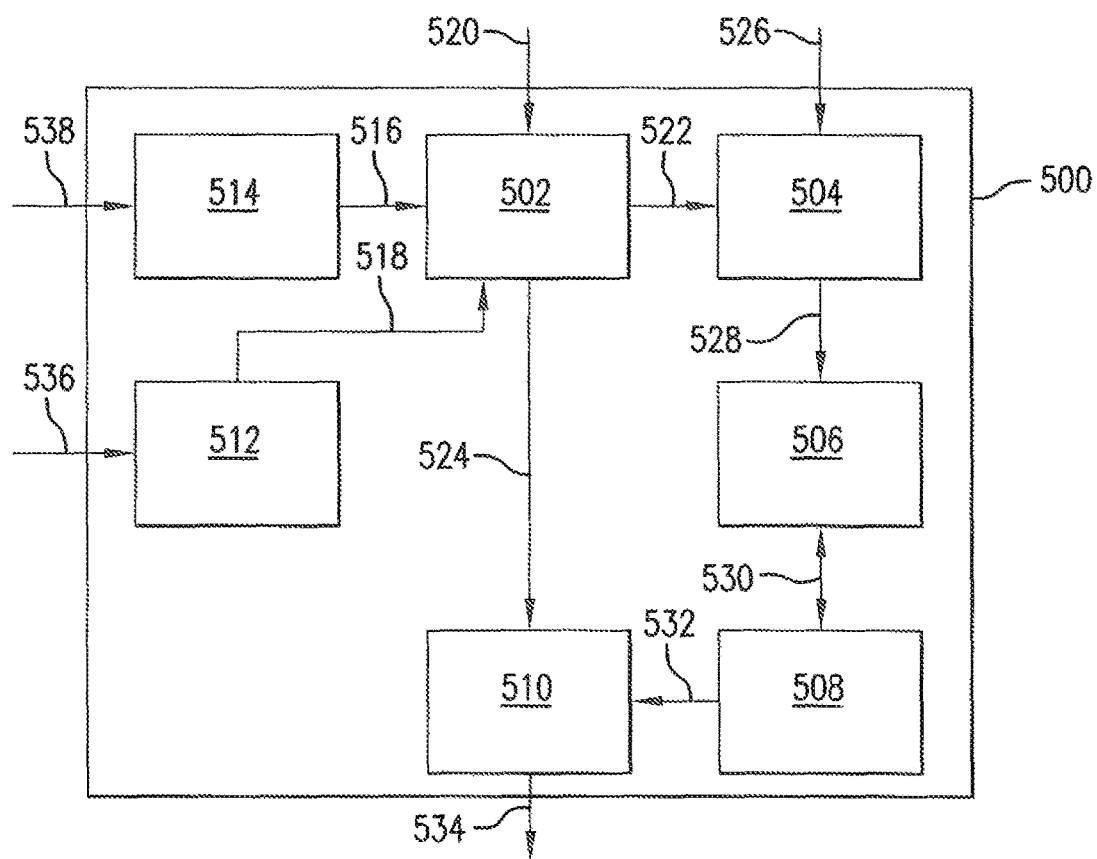
FIG. 5 illustrates a device to receive and transmit exercise data in accordance with aspects of the present invention.

FIG. 5 illustrates a component 500 of shoes 104 of FIG. 1 that receive and transmit exercise data in accordance with aspects of the present invention.

As shown in the figure, component 500 includes a wake up component 502, a receiver 504, a memory 506, a processing component 508, a transmitter 510, a user interface 512, and a positioning system 514.

As shown in the figure, wake up component 502, receiver 504, memory 506, processing component 508, transmitter 510, user interface 512, and positioning system 514 are shown as distinct devices. In some embodiments, at least two of wake up component 502, receiver 504, memory 506, processing component 508, transmitter 510, user interface 512, and positioning system 514 may be combined as a unitary device. In some embodiments, at least one of wake up component 502, receiver 504, memory 506, processing component 508, transmitter 510, user interface 512, and positioning system 514 may be implemented as a computer having tangible computer-readable media for carrying or having computer-executable instructions or data structures stored thereon. Such tangible computer-readable media can be any available media that can be accessed by a general purpose or special purpose computer. Non-limiting examples of tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. For information transferred or provided over a network or another communications connection (either hardwired, wireless, or a combination of hardwired or wireless) to a computer, the computer may properly view the connection as a computer-readable medium. Thus, any such connection may be properly termed a computer-readable medium. Combinations of the above should also be included within the scope of computer-readable media.

Wake up component 502 receives wake up signals by communicating with positioning system 514 via a channel 516, user interface 512 via a channel 518, or exercise equipment via a channel 520. Wake up component 502 also communicates with receiver 504 via a channel 522 and transmitter 510 via a channel 524.

Receiver 504 additionally receives data signals from exercise equipment related to exercise data via a channel 526 and provides the data signals to memory 506 via a channel 528.

Memory 506 additionally provides data signals to processing component 508 via a channel 530. Memory 506 may be any device or system that is able to receive, store, retrieve and manage data, non-limiting examples of which include random access memory (RAM), static RAM (SRAM), dynamic RAM (DRAM), flash, disk, etc.

Processing component 508 receives data signals from memory 506 via channel 530 and generates user data based on the data signals, and provide the user data to transmitter 510 via a channel 532.

Transmitter 510 additionally sends and/or receives transmissions via a channel 534 based on the communications with wake up component 502 and processing component 508.

The user interacts with user interface 512 via a channel 536 when the user is near an exercise machine, and user interface 512 provides that information to wake up component 502.

Positioning system 514 determines when shoes 104 are near an exercise machine via a channel 538 and provides that information to wake up component 502 via channel 516. Positioning system 514 may be any known system or device that is able to determine a location of shoes 104. A non-limiting example of a position system 514 includes a GPS enabled system that determines the geodetic locations of shoes 104 and exercise equipment.

Each of channels 516, 518, 520, 522, 524, 526, 528, 530, 532, 534, 536 and 538 may be any known type of wired or wireless communication channel.

The interaction between wake up component 502, receiver 504, memory 506, processing component 508, transmitter 510, user interface 512, and positioning system 514 will be further described with reference to FIG. 6.

Figure 6:
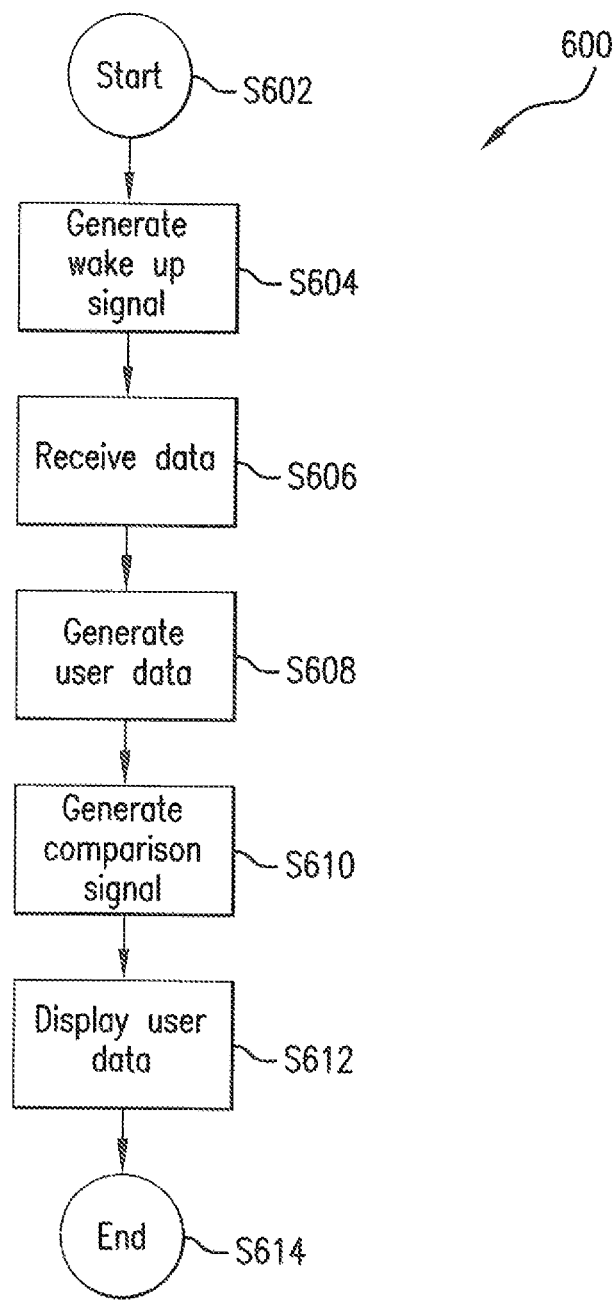
FIG. 6 illustrates a process by which exercise data is received and transmitted in accordance with aspects of the present invention.

FIG. 6 illustrates a process 600 by which exercise data is received and transmitted, in accordance with aspects of the present invention. For purposes of discussion, presume that a user has performed various activities and/or exercises, the data for which has been stored on a user's smart wearable device. As a non-limiting example, the user may have run 2 miles on a treadmill, then biked 10 miles on a stationary bike, and then lifted weights. After completing the various activities, the user desires to see the recorded data for the day, and the user may also desire to see how the recorded data for the day compares to data previously recorded. The wearable device has received and stored the data from all activities, and data from each activity has a signal based on the type of activity. The user wants to see the data in a manner that is easy to understand. In some embodiments, the data is transferred to an intermediate device, like a mobile phone, as a first step, and then the data is transferred from the intermediate device to another device, like a computer. In other embodiments, the recorded data is transferred directly from the wearable device to the computer. Regardless of the location of the data, FIG. 6 illustrates an example process of how the data may be transferred.

As shown in the figure, process 600 starts (S602) and a wake up signal is generated (S604). For example, returning to FIG. 1, treadmill 102 is sending handshake signals in attempt to connect with a wearable device. A handshake is required to initiate a connection between two or more devices. The handshake signals broadcast and transmitted may be any known handshake protocol.

As user 100 approaches treadmill 102, shoes 104 enter the area in which the handshake signals emitted by treadmill 102 reach shoes 104. The area in which the handshake signal can reach shoes 104 may change based on how many other pieces of equipment are in the area. For example, in a crowded health club, the handshake signal may only reach shoes 104 after user 100 steps on treadmill 102. As another example, in an individual's home, the handshake signal may reach shoes 104 when the user is within 10 feet of treadmill 102.

Referring back to FIG. 5, wake up component 502 receives the handshake signal from treadmill 102 via channel 520. Wake up component 502 then generates and transmits a wake up signal to receiver 504 via channel 522.

In another embodiment, shoes 104 may be equipped with user interface 512. User 100 can interact with user interface 512 when user 100 is on or near treadmill 102. User interface 512 would then notify wake up component 502 via channel 518 to generate a wake up signal and send it to receiver 504 via channel 522. The interaction between user 100 and user interface 512 may occur via a button, switch, graphical user interface, numeric keypad, or any other type of interface that would allow user 100 to communicate with user interface 512. As a non-limiting example, when the user is preparing to run on a treadmill, he may press a button on his wearable device. Pressing the button may notify wake up component 502, which generates a wake up signal and sends it to receiver 504.

In yet another embodiment, shoes 104 may be equipped with positioning system 514. Positioning system 514 is operable to provide the geodetic location of shoes 104, and to detect the proximity of shoes 104 to the geodetic location of an exercise apparatus, such as treadmill 102. Positioning system 514 may be any device or system that is able to determine a location of shoes 104. A non-limiting example of positioning system 514 includes one that uses a global positioning system (GPS) via channel 538 to determine the proximity of shoes 104 to treadmill 102. When positioning system determines 514 that shoes 104 are within a certain, predetermined distance of treadmill 102, positioning system 514 notifies wake up component 502 via channel 516 to generate a wake up signal and sent it to receiver 504.

Returning to FIG. 6, after a wake up signal is generated (S604), activity data is then received (S606). For example, referring back to FIG. 1, as user 100 is running on treadmill 102, treadmill 102 is sending data signals related to treadmill activity levels of user 100 to shoes 104 via wireless connection 106. In the example as shown in FIG. 2, as user 100 is riding stationary bike 202, stationary bike is sending data signals related to stationary bike activity levels of user 100 to shoes 104 via wireless connection 204.

Referring to FIG. 5, receiver 504 receives data signals from a piece of exercise equipment used by user 100. Receiver 504 then provides data signals from the piece of exercise equipment to memory 506, which stores the data provided by the signals.

In some embodiments, the data from each piece of exercise equipment is stored separately within memory 506 such that the user can view data associated with a single piece of exercise equipment (for example, how far the user ran on treadmill 102). In other embodiments, the data from one or more pieces of exercise equipment is combined such that the user can view the totals from the data received from each piece of equipment (for example, how many total calories the user burned during the day).

Returning to FIG. 6, after the activity data is received (S606), user data is then generated (S608). For example, referring to FIG. 5, memory 504 provides downloaded data signals to processing component 508. Processing component 508 may generate user data in multiple ways. In one embodiment, processing component 508 may generate user data based on the data signals received from each piece of exercise equipment. In another embodiment, processing component 508 may generate user data based on functions of the data signals received from each piece of exercise equipment. After generating user data, processing component 508 may provide the user data to memory 506.

Returning to FIG. 6, after the user data is generated (S608), a comparison signal is then generated (S610). For example, returning to FIG. 5, processing component 508 notifies memory 506 that it is looking for specific user data for comparison.

In some embodiments, the user may predetermine what kind of user data processing component 508 is looking for from memory 506, or there may be a default setting that prompts processing component 508 to gather user data from a specific time period. As a non-limiting example, the user may program the system to automatically compare the total number of calories burned today to the total number of calories burned yesterday.

In other embodiments, component 500 may automatically compare the treadmill activity for the past month. Memory 506 then provides processing component 508 with the requested data and/or data signals so that processing component can execute the user commands to create a comparison signal.

As a non-limiting example, presume that: at a time $t_1$, the user downloads data from treadmill 102, stationary bike 202, and weightlifting apparatus 302; at a time $t_2$, the user downloads data from stationary bike 202 and weightlifting apparatus 302; and at a time $t_3$, the user downloads data from treadmill 102, stationary bike 202, and weightlifting apparatus 302.

In some embodiments, in creating comparison signals, processing component 508 generates a comparison signal between comparable data sets. In the above example, processing component 508 may generate a comparison signal based on the combination of data from all three pieces of exercise equipment from times $t_1$ and $t_3$, but the data from $t_2$ would not be available for comparison because there is no data available from treadmill 102 at time $t_2$. Processing component 508 may generate a comparison signal based on data from stationary bike 202 and weightlifting apparatus 302 at times $t_1$, $t_2$, and $t_3$ because data is available for those wearable at all three times.

Returning to FIG. 6, after a comparison signal is generated (S610), the user data is displayed (S612). For example, referring to FIG. 5, processing component 508 provides the comparison signal to transmitter 510, and transmitter 510 transmits the comparison signal to an external device. The comparison signal may be transmitted by any known manner by which data transmission may occur, non-limiting examples of which include via wireless interact, Bluetooth, radio frequency (RF), or GPS.

Returning to FIG. 4, after working out, user 100 may return home and shoes 104 may come in close proximity with either mobile phone 402 or computer 404. Shoes 104 may then connect with mobile phone 402 or computer 404 using one of the methods previously described (handshake exchange, positioning system, or user interface).

Returning to FIG. 5, wake up component 502 notifies transmitter 510 to transmit the comparison signal to mobile phone 402 and/or computer 404. Returning to FIG. 4, user 100 may then see the comparison of exercise activities on mobile phone 402 and/or computer 404. As a non-limiting example, if user 100 burned 150 more calories today than yesterday, mobile phone 402 and/or computer 404 would show user 100 that he burned 150 more calories today than yesterday.

Returning to FIG. 6, at this point, process 600 ends (S614).

In the above discussed example embodiment, a single wearable device is used to store activity data from a plurality of different activities. In another embodiment, user 100 may use multiple wearable devices when performing multiple exercises. Each device may receive data from only a single exercise machine, or each device may receive specific data from all exercise machines. In either case, when user 100 is near mobile device 402 or computer 404, data from the wearable devices is downloaded and displayed as previously described.

The instant invention provides a device and method to wirelessly download data from exercise machines to a wearable device. The wearable device is able to compare exercise and activity data from previous days or previous exercise sessions to notify the user of his progress.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A wearable device for use by a user, the wearable device comprising:
   a positioning system operable to provide a geodetic location of the wearable device;
   a wake up component operable to generate a wake-up signal when the geodetic location of the wearable device is within a predetermined distance of an exercise activity location;
   a transceiver operable to receive an exercise signal from a transmitter based on receipt of the wake-up signal, the exercise signal being associated with an exercise session of the user; and
   a memory operable to store the exercise data based on the exercise signal;
   wherein the transceiver is further operable to transmit an exercise download signal based on the exercise data.

2. The device of claim 1, wherein the wake up component is operable to generate the wake-up signal upon receipt of a handshake signal originating from the transmitter at an exercise equipment at the detected exercise activity location.

3. The device of claim 1, further comprising a processing component operable to generate user data based on at least one of a first combination and a second combination, the first combination being based on the exercise signal, and the second combination being based on the exercise data.

4. The device of claim 3,
   wherein the processing component is operable to generate the user data as a first signature;
   wherein the memory has a second signature stored therein;
   wherein the processing component is further operable to generate a comparison signal based on a comparison of the first signature and the second signature; and
   wherein the transceiver is further operable to transmit the comparison signal.

5. The device of claim 1, wherein the transceiver is operable to receive and/or transmit via at least one of: a Bluetooth signal, a Wi-Fi signal and an RF signal.

6. The device of claim 1, wherein the transceiver is configured to transmit the exercise download signal to a user device in communication with the wearable device.

7. The device of claim 6, wherein the wearable device comprises at least one computerized apparatus disposed at a shoe and the user device comprises a mobile telephone apparatus.

8. A smart shoe apparatus to be worn by a user:
   a positioning apparatus configured to provide a geodetic location of the smart shoe apparatus;
   a wake-up component configured to generate a wake-up signal when the geodetic location of the smart shoe is within a predetermined distance of an activity location;
   a transceiver apparatus configured to receive an activity signal from a transmitter based at least in part on receipt of the wake-up signal thereat, and the activity signal being associated with an activity session of the user; and
   a memory apparatus operable to store activity data based at least in part on the activity signal;
   wherein the transceiver apparatus is further configured to transmit an activity download signal based at least in part on the activity data.

9. The smart shoe of claim 8, wherein the positioning apparatus comprises a global positioning system (GPS)-enabled apparatus.

10. The smart shoe of claim 8, wherein the transmitter is associated to exercise equipment.

11. The smart shoe of claim 8, wherein the transceiver is configured to transmit the exercise download signal to a mobile user device in communication with the smart shoe.

12. The smart shoe of claim 11, wherein the transmission of the activity download signal occurs when the positioning apparatus determines that the smart shoe is within a predetermined distance to the mobile user device.

13. The smart shoe of claim 8, wherein the activity download signal comprises a signal to transmit the stored activity data to a user device in communication with the smart shoe for comparison with previously downloaded and stored activity data at the user device.

14. The smart shoe of claim 8, wherein the transceiver is operable to receive and/or transmit via at least one of: a Bluetooth signal, a Wi-Fi signal and an RF signal.

15. A wearable device for use by a user, the wearable device comprising:
   a user interface operable to generate a user command based on a user action;

a wake up component operable to generate a wake-up signal based on a user action at an exercise activity location;

a receiver operable to receive an exercise signal from a transmitter based on receipt of the wake-up signal, the exercise signal being associated with an exercise session of the user;

a memory operable to store exercise data based on the exercise signal and to store a first signature;

a processing component operable to:

generate user data as a second signature, the user data being based on at least one of: a first combination based on the exercise signal and a second combination based on the exercise data; and generate a comparison signal based on a comparison of the first signature and the second signature; and a transmitter operable to transmit an exercise download signal based on the exercise data and to transmit the comparison signal.

16. The device of claim 8, wherein the receiver and the transmitter are operable to receive and/or transmit via at least one of: a Bluetooth signal, a Wi-Fi signal and an RF signal.

17. The device of claim 8, wherein the wearable device comprises at least one shoe having a computerized apparatus associated therewith.

18. The device of claim 8, wherein the first and second transmitters are associated to first and second exercise equipment, respectively.

19. The device of claim 8, wherein the exercise download signal comprises a signal to transmit the exercise data and the comparison signal to a user device in communication with the smart shoe for display thereat.

20. The device of claim 8, further comprising a positioning apparatus configured to provide a geodetic location of the smart shoe apparatus; and the wake up component is operable to generate the wake-up signal when the geodetic location of the wearable device is within a predetermined distance of the exercise activity location.

* * * * *